(12) United States Patent
Shang

(10) Patent No.: US 10,588,514 B1
(45) Date of Patent: Mar. 17, 2020

(54) VIVO PHOTON ANALYSIS SYSTEM AND METHOD

(71) Applicant: Hua Shang, Shanghai (CN)

(72) Inventor: Hua Shang, Shanghai (CN)

( * ) Notice: Subject to any disclaimer, the term of this patent is extended or adjusted under 35 U.S.C. 154(b) by 0 days.

(21) Appl. No.: 16/397,010

(22) Filed: Apr. 29, 2019

(51) Int. Cl.
*A61B 5/00* (2006.01)

(52) U.S. Cl.
CPC .......... *A61B 5/0084* (2013.01); *A61B 5/0071* (2013.01); *A61B 5/742* (2013.01); *A61B 5/4088* (2013.01)

(58) Field of Classification Search
CPC .......... G02B 7/002; G02B 3/08; G02B 27/30; A61B 2562/0219; A61B 2562/0238; A61B 2562/046; A61B 2562/146; A61B 2562/185
USPC ........................................ 600/476–480, 407
See application file for complete search history.

(56) References Cited

U.S. PATENT DOCUMENTS

| | | | | |
|---|---|---|---|---|
| 4,612,938 A | * | 9/1986 | Dietrich | A61B 1/06 356/241.1 |
| 4,981,138 A | * | 1/1991 | Deckelbaum | A61B 5/0071 600/477 |
| 5,318,024 A | * | 6/1994 | Kittrell | A61B 1/00096 600/478 |
| 5,452,723 A | * | 9/1995 | Wu | A61B 5/0059 250/339.01 |
| 5,459,570 A | * | 10/1995 | Swanson | A61B 1/00096 356/479 |
| 5,549,596 A | * | 8/1996 | Latina | A61F 9/008 606/4 |
| 6,608,717 B1 | * | 8/2003 | Medford | A61B 5/0066 356/479 |
| 6,697,665 B1 | * | 2/2004 | Rava | A61B 5/0071 600/475 |
| 6,753,966 B2 | * | 6/2004 | Von Rosenberg | G01J 3/02 356/432 |
| 6,788,967 B2 | * | 9/2004 | Ben-Haim | A61N 1/36564 600/374 |

(Continued)

*Primary Examiner* — Oommen Jacob
(74) *Attorney, Agent, or Firm* — Merchant & Gould P.C.

(57) ABSTRACT

The present invention provides an in vivo photon analysis system and method, wherein the system comprises: an in vivo device and an in vitro device; the in vivo device comprises: an intervention function module which enters into a human body, outputs a laser output by the in vitro device to a preset position, and acquires a feedback fluorescence of the preset position; the in vitro device comprises: a laser light source module which outputs a first group of laser and a second group of laser; a coupling and switching module which couples the first group of laser to obtain a first to-be-output laser, couples the second group of laser to obtain a second to-be-output laser, acquires the feedback fluorescence, and sends the feedback fluorescence to an analyzing and testing module; an analyzing and testing module which receives the feedback fluorescence, and analyzes the feedback fluorescence, so as to obtain analysis results of the feedback fluorescence, and send the analysis results of the feedback fluorescence to a core processing module; and a core processing module which controls the laser light source module to output the first group of laser, and controls the laser light source module to output the second group of laser according to the analysis results of the feedback fluorescence.

6 Claims, 2 Drawing Sheets

(56) References Cited

U.S. PATENT DOCUMENTS

| | | | | |
|---|---|---|---|---|
| 7,970,458 | B2* | 6/2011 | Norris | A61B 1/00172 600/478 |
| 8,914,098 | B2* | 12/2014 | Brennan | A61B 5/418 600/478 |
| 8,964,017 | B2* | 2/2015 | Vertikov | A61B 5/0066 348/65 |
| 2001/0047137 | A1* | 11/2001 | Moreno | A61B 5/0075 600/475 |
| 2008/0255461 | A1* | 10/2008 | Weersink | A61B 5/0084 600/476 |
| 2010/0228124 | A1* | 9/2010 | Brennan | A61B 5/0066 600/437 |
| 2010/0228238 | A1* | 9/2010 | Brennan | A61B 5/0073 606/13 |

* cited by examiner

VIVO PHOTON ANALYSIS SYSTEM AND METHOD

TECHNICAL FIELD

The present invention relates to the field of interventional radiology, in particular to an in vivo photon analysis system and method.

BACKGROUND ART

Photon diagnosis and photon therapy belong to two research and application development directions in the current medical photon technology, with the former taking a photon as an information carrier, and the latter taking a photon as an energy carrier. In photon diagnosis, identification of different tissues can be realized through performing real-time detection or imaging on reflected lights, transmission lights and scattered lights in the tissue or on fluorescent lights (including auto fluorescence and drug fluorescence) generated after a tissue is excited by an exciting light. In photon diagnosis, tissues are analyzed according to optical properties owned by a biological tissue. Compared with traditional surgical biopsy, photon diagnosis is a non-invasive histopathological analysis method, and can overcome a change in biochemical properties of tissues which may be caused in a surgical biopsy process; compared with such examinations as X-rays, CT and MRI, photon diagnosis can not only avoid ionizing radiation, but also realize early diagnosis of pathology. Photon therapy includes intense laser therapy, low-level (low-intensity) laser therapy and photodynamic therapy (PDT). With low-level laser radiation as an example, after an organism is radiated by a low-level laser, the laser does not directly cause an irreversible damage of a biological tissue, however, due to its own biological stimulus effect, a radiated tissue generates a "responsive" response to this stimulus. On a molecular level, synthesis of protein and nucleic acid is adjusted, replication of DNA is influenced, and the function of enzyme is adjusted; and on a cellular level, it is a process of removing pathology through mobilization, compensation, nutrition, repairing, immunity and other regenerative or defense mechanisms.

In recent years, along with an increasing maturity of nanotechnology and related interdisciplines, an application of the nanotechnology in medical science has revealed its importance for the first time. Many molecular markers which are applied to diagnostics and therapeutics respectively are integrated to form theranostics. Based on an important role of a photon technology in medical diagnosis and therapy, photonic theranostics, a brand-new research direction, is gradually formed, which is also a trend towards medical personalized development in the future. With photodynamic therapy (PDT) as an example, the target is to develop a nano particle platform which takes photosensitizer molecules as a core. The platform integrates active targeting delivery of medicines, diagnosis of tumors (such as MRI and molecular fluorescence imaging), therapy (hyperthermia therapy and PDT), dose monitoring (singlet oxygen probes and oxygen molecule probes), and therapeutic effect evaluation (cell apoptosis probes, MRI and biochemiluminescence), thereby fully reflecting advantages and potential applications of modern nanomedicine.

As an important means of diagnosis and therapy, the biggest drawback of photon is that visible lights and near-infrared lights cannot penetrate deep into human tissues, and now diagnosis and therapy can only be performed on a body surface and on surfaces of larger cavities of a human body (for example, esophagus). In order to solve the problem, a photon diagnosis and therapy device and method, which can penetrate deep into a human body and reach a lesion site and which will not cause greater damages to the human body, are needed.

SUMMARY OF THE INVENTION

The present invention aims at providing an in vivo photon analysis system and method for overcoming the above problem or at least partially solving the above problem.

In order to achieve the above objective, technical solutions of the present invention are realized specifically as follows:

One aspect of the present invention provides an in vivo photon analysis system, including: an in vivo device and an in vitro device; wherein the in vivo device includes: an intervention function module; the intervention function module is configured to enter into a human body, output a laser output by the in vitro device to a preset position, and acquire a feedback fluorescence of the preset position; the in vitro device includes: a core processing module, a displaying and recording module, a laser light source module, an analyzing and testing module, and a coupling and switching module; the laser light source module is configured to output a first group of laser and a second group of laser, wherein the first group of laser includes a laser of at least one wavelength, and the second group of laser includes a laser of at least one wavelength; the coupling and switching module is configured to couple the first group of laser to obtain a first to-be-output laser, and send the first to-be-output laser to the intervention function module, and is configured to couple the second group of laser to obtain a second to-be-output laser, and send the second to-be-output laser to the intervention function module, so as to acquire the feedback fluorescence, and send the feedback fluorescence to the analyzing and testing module; the analyzing and testing module is configured to receive the feedback fluorescence, and analyze the feedback fluorescence, so as to obtain analysis results of the feedback fluorescence, and send the analysis results of the feedback fluorescence to the core processing module; and the core processing module is configured to control the laser light source module to output the first group of laser, and control the laser light source module to output the second group of laser according to the analysis results of the feedback fluorescence.

Wherein the in vitro device further includes: a displaying and recording module; the displaying and recording module is configured to receive the analysis results of the feedback fluorescence obtained by the analyzing and testing module, and display and record the analysis results of the feedback fluorescence.

Wherein the laser light source module is further configured to output a third group of laser, wherein the third group of laser includes a laser of at least one wavelength; the analyzing and testing module is further configured to acquire the first to-be-output laser, analyze the first to-be-output laser to obtain analysis results of the first to-be-output laser, and send the analysis results of the first to-be-output laser to the core processing module; the core processing module is further configured to control the laser light source module to output a third group of laser according to analysis results of the first to-be-output laser; and the coupling and switching module is configured to couple the third group of laser to obtain a third to-be-output laser, and send the third to-be-output laser to the intervention function module.

Wherein the in vitro device further includes: a displaying and recording module; the displaying and recording module is configured to receive analysis results of the first to-be-output laser obtained by the analyzing and testing module, and display and record analysis results of the first to-be-output laser.

Another aspect of the present invention provides an in vivo photon analysis method, including: the core processing module controls the laser light source module to output the first group of laser, wherein the first group of laser includes a laser of at least one wavelength; the laser light source module outputs the first group of laser; the coupling and switching module couples the first group of laser to obtain a first to-be-output laser, and sends the first to-be-output laser to the intervention function module; the intervention function module enters into a human body, outputs a laser output by the coupling and switching module to a preset position, and acquires a feedback fluorescence of the preset position; the analyzing and testing module receives the feedback fluorescence, and analyzes the feedback fluorescence, so as to obtain analysis results of the feedback fluorescence, and sends the analysis results of the feedback fluorescence to the core processing module; the core processing module controls the laser light source module to output the second group of laser according to the analysis results of the feedback fluorescence, wherein the second group of laser includes a laser of at least one wavelength; the laser light source module outputs the second group of laser; and the coupling and switching module couples the second group of laser to obtain a second to-be-output laser, and sends the second to-be-output laser to the intervention function module. Then return to perform the steps of enabling the intervention function module to enter into a human body, outputting a laser output by a coupling and switching device to a preset position, and acquiring a feedback fluorescence of the preset position.

Wherein the method further includes: the displaying and recording module receives analysis results of the feedback fluorescence obtained by the analyzing and testing module, and displays and records the analysis results of the feedback fluorescence.

Wherein the method further includes: the analyzing and testing module acquires the first to-be-output laser, analyzes the first to-be-output laser to obtain analysis results of the first to-be-output laser, and sends the analysis results of the first to-be-output laser to the core processing module; the core processing module controls the laser light source module to output a third group of laser according to analysis results of the first to-be-output laser, wherein the third group of laser includes a laser of at least one wavelength; the laser light source module outputs the third group of laser; and the coupling and switching module couples the third group of laser to obtain a third to-be-output laser, and sends the third to-be-output laser to the intervention function module.

Wherein the method further includes: the displaying and recording module receives the analysis results of the first to-be-output laser obtained by the analyzing and testing module, and displays and records the analysis results of the first to-be-output laser.

It can be seen that, an in vivo photon analysis system and method provided by the present invention can penetrate deep into a human body through vascular tunnels inside a human body via a minimally invasive manner, penetrate through a vascular wall and enter into human tissues, extract tissue samples and spectral information of the lesion site, and perform a light therapy on pathological tissues, thereby playing a role of diagnosis and therapy.

BRIEF DESCRIPTION OF THE DRAWINGS

In order to more clearly describe technical solutions of embodiments of the present invention, a brief introduction will be made to the accompanying drawings which need to be used in the description of the embodiments. Apparently, the accompanying drawings described below are merely some embodiments of the present invention, and for those skilled in the art, other accompanying drawings can be obtained based on these accompanying drawings without any creative effort.

DETAILED DESCRIPTION OF THE EMBODIMENTS

Exemplary embodiments of the present disclosure will be described in detail below with reference to accompanying drawings. Although exemplary embodiments of the present disclosure have been displayed in the accompanying drawings, however, it should be understood that, the present disclosure can be realized in various forms, and should not be limited by embodiments described herein. In contrary, these embodiments are provided for a more thorough understanding of the present disclosure, and can completely convey the scope of the present disclosure to those skilled in the art.

Figure 1:
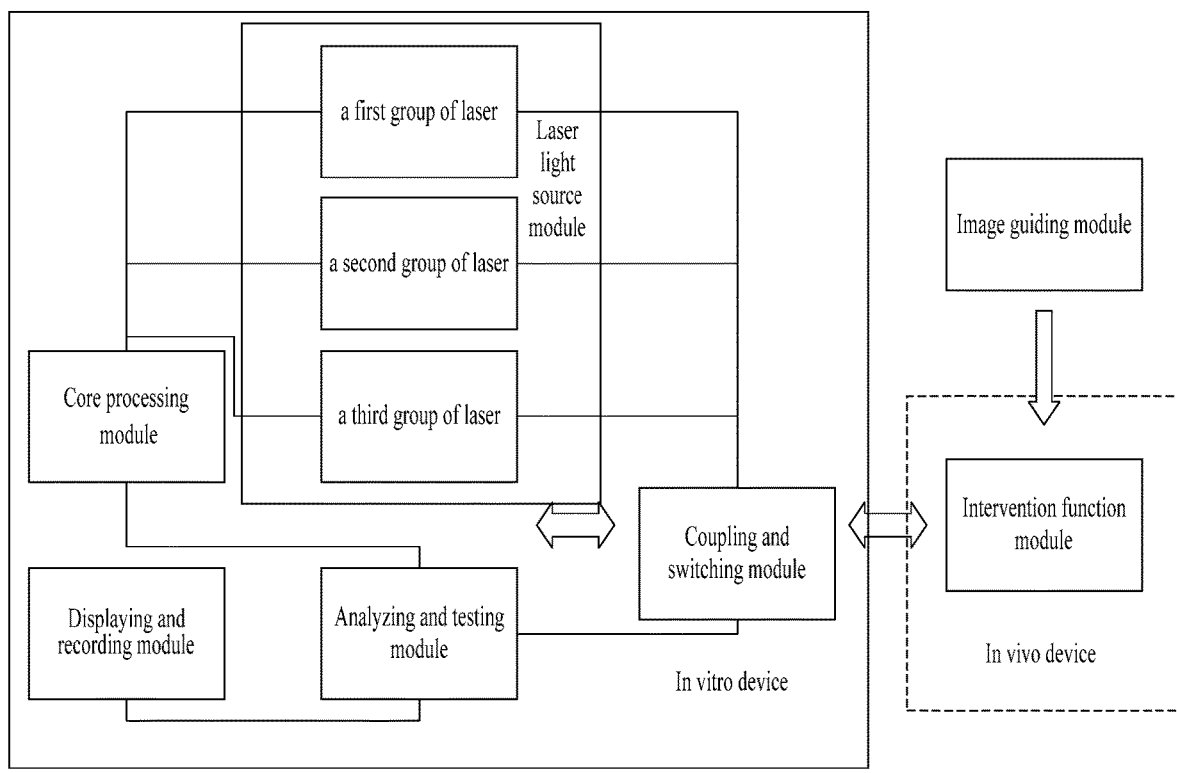
FIG. 1 is a structural schematic diagram of an in vivo photon analysis system provided by an embodiment of the present invention.

FIG. 1 shows a structural schematic diagram of an in vivo photon analysis system provided by an embodiment of the present invention. Please refer to FIG. 1, and an in vivo photon analysis system provided by the embodiment of the present invention includes:

an in vivo device includes: an intervention function module;

the intervention function module is configured to enter into a human body, output a laser output by the in vitro device to a preset position, and acquire a feedback fluorescence of the preset position;

an in vitro device includes: a core processing module, a displaying and recording module, a laser light source module, an analyzing and testing module, and a coupling and switching module;

the laser light source module is configured to output a first group of laser and a second group of laser, wherein the first group of laser includes a laser of at least one wavelength, and the second group of laser includes a laser of at least one wavelength;

the coupling and switching module is configured to couple the first group of laser to obtain a first to-be-output laser, and send the first to-be-output laser to the intervention function module, and is configured to couple the second group of laser to obtain a second to-be-output laser, and send the second to-be-output laser to the intervention function module, so as to acquire the feedback fluorescence, and send the feedback fluorescence to the analyzing and testing module;

the analyzing and testing module is configured to receive the feedback fluorescence, and analyze the feedback fluorescence, so as to obtain analysis results of the feedback fluorescence, and send the analysis results of the feedback fluorescence to the core processing module; and the core processing module is configured to control the laser light source module to output the first group of laser, and control the laser light source module to output the second group of laser according to the analysis results of the feedback fluorescence.

Specifically, a core processing module, a laser light source module, an analyzing and testing module and a coupling and switching module constitute an in vitro device; and an intervention function module forms an in vivo device, and can enter inside a human body under an assistance of an image guiding module. In addition, the in vitro device can further include a displaying and recording module.

Wherein, the core processing module is provided with a microprocessor, and the core processing module can perform unified management and control on a displaying and recording module, a laser light source module, and an analyzing and testing module, and performs advanced treatment on the analysis data.

A laser light source module includes but is not limited to laser light sources of a single wavelength or of multiple wavelengths, and an output mode is continuous waves or nanosecond/picosecond/femtosecond pulses, so as to acquire absorption/fluorescence spectral information of tissue irradiation. Specifically, the laser light source module can contain multiple laser devices which can emit multiple wavelengths, for example, the wavelengths are respectively 532 nm, 630 nm and 650 nm, so as to be adapted to diagnosis and therapy of different diseases.

An analyzing and testing module includes but is not limited to a spectrograph, a spectrophotometer, and a power meter, and is configured to analyze and process laser or fluorescence information returned back by an intervention function module. Specifically, the analyzing and testing module can be constituted by a fiber optic spectrometer and other instruments. The fiber optic spectrometer performs spectrum analysis on returned lights received by the intervention function module. The fiber optic spectrometer can be added with a wave filter which filters wavelengths of output lasers, thereby improving sensitivity in collecting fluorescence wavelengths.

A coupling and switching module is a device connecting a laser light source module, an analyzing and testing module and an intervention function module, and is constituted by an optical fiber coupler, a beam splitter, an isolator and a light filter. Specifically, the coupling and switching module can be constituted by an optical fiber coupler. One construction mode of the coupling and switching module is a two-level structure, wherein a first level of structure is a structure which unifies N into one (N is greater than or equal to 2), that is, lasers of each wavelength emitted by N laser devices are coupled to one optical fiber for transmission; a second level of structure is a structure which unifies two into one, that is, lasers of multiple wavelengths and optical fibers of the analyzing and testing module are coupled to one optical fiber; and the connected light function guide wire is internally provided with an optical fiber core wire. Another construction mode of the coupling and switching module is a one-level structure, wherein N optical fibers (N is greater than or equal to 2) are coupled to a light function guide wire. Among the N optical fibers, N−1 optical fibers are fibers output by a multi-wavelength laser array, and one optical fiber is an optical fiber of an analyzing and testing module; and the connected light function guide wire is internally provided with N optical fiber core wires.

An intervention function module includes but is not limited to various light function guide wires, intravascular puncture needles, and plays a role of guiding lights into a human body for therapy and sampling of tissues; wherein light function guide wires include a first light function guide wire and a second light function guide wire, which are respectively light function guide wires used for diagnosis and therapy. Specifically, the intervention function module further includes a series of changeable endovascular interventional instruments which include light function guide wires (used for diagnosis/therapy) and intravascular puncture needles. Light function guide wires play a role of bidirectional transmission of photons, can penetrate through vascular tunnels, and have a proper strength and flexibility, thereby avoiding optical fiber breakage inside the human body or avoiding damage to human tissues. In the present invention, in one case, a light function guide wire has a diameter of 50 μm to 500 μm and a length of 0.5 m to 2 m. A light function guide wire is internally provided with optical fibers, meshy or spirally incised metal materials are wrapped outside the light function guide wire, and a hydrophilic or hydrophobic coating is coated on the outermost layer, so as to increase blood compatibility. A tail end of a light function guide wire further includes a light-transmitting structure which releases laser from a top end or a side face of a guide wire. The tail end of a light function guide wire is further provided with a vascular puncture needle, wherein a head part of the vascular puncture needle is cut into a multivalve structure through a memory metal, and the lasers, conducted by an optical fiber inside a vascular puncture needle, are deformed and expanded after being heated, thereby expanding puncture wounds; after heating is stopped, the lasers are contracted together, so as to grab tissue cells. Under another case, a light function guide wire has an external diameter of 400 μm, is internally provided with four optical fiber core wires with a diameter of 50 μm, and the outer layer is wrapped with stainless metal tubes with spiral slits. The above metal tube is externally coated with a hydrophilic coating, for example, polytetrafluoroethylene, silicone rubber, polyethylene, polyvinyl chloride, fluorocarbon polymer and polyurethane. The light function guide wire is connected with a laser array and a spectrograph through an optical fiber coupler, three optical fiber core wires inside the wrapped optical fiber guide wire are respectively connected with three laser devices, while another optical fiber core wire inside the wrapped optical fiber guide wire is connected with a spectrograph. The lasers output by a laser device are emitted through three optical fiber core wires inside the optical fiber guide wire, and are collected by another optical fiber core wire and transmitted back to a spectrograph.

An image guiding module includes but is not limited to an X-ray, an ultrasound, CT and MRI, and is responsible for guiding an instrument in an intervention function module to enter into a blood vessel and reach a lesion site.

As an optional implementation of an embodiment of the present invention, an in vitro device further includes: a displaying and recording module, wherein the displaying and recording module is configured to receive analysis results of the feedback fluorescence obtained by the analyzing and testing module, and display and record the analysis results of the feedback fluorescence. Specifically, the displaying and recording module includes but is not limited to a display screen, a printer, a hard disk and an external storage device. Therefore, analysis results of the feedback fluorescence can be displayed and recorded, so as to facilitate follow-up view and analysis of medical staff.

As an optional implementation of an embodiment of the present invention, the laser light source module is further configured to output a third group of laser, wherein the third group of laser includes a laser of at least one wavelength; the analyzing and testing module is further configured to acquire the first to-be-output laser, analyze the first to-be-output laser to obtain analysis results of the first to-be-output laser, and send the analysis results of the first to-be-output laser to the core processing module; the core processing module is further configured to control the laser light source module to output the third group of laser according to analysis results of the first to-be-output laser; and the coupling and switching module is configured to couple the third group of laser to obtain a third to-be-output laser, and send the third to-be-output laser to the intervention function module. Therefore, lasers of different wavelengths for light therapy can be provided according to different situations.

As an optional implementation of an embodiment of the present invention, an in vitro device further includes a displaying and recording module which is configured to receive analysis results of the first to-be-output laser obtained by the analyzing and testing module, and display and record analysis results of the first to-be-output laser, so as to display and record analysis results of the first to-be-output laser, and facilitate follow-up view and analysis of medical staff.

It can be seen that, an in vivo photon analysis system provided by the present invention can penetrate deep into a human body through vascular tunnels inside a human body via a minimally invasive manner, penetrate through a vascular wall and enter into human tissues, extract tissue samples and spectral information of the lesion site, and perform a light therapy on pathological tissues, thereby playing a role of diagnosis and therapy.

Three specific embodiments will be provided below to describe an in vivo photon analysis system provided by embodiments of the present invention, however, the present invention is not limited hereto:

Embodiment 1

With fluorescence diagnosis as an example, through percutaneous puncture of a blood vessel and under guidance of clinical imaging, an optical fiber guide wire passes through a blood vessel and is guided to a lesion site. A laser device of 630 nm is selected by a controller to emit light. The laser passes through the optical fiber guide wire and irradiates on a lesion tissue, and the generated fluorescence is collected by an optical fiber guide wire and is transmitted back to an optical fiber spectrograph. Such feature parameters as peak wavelength of fluorescence emission, relative fluorescence strength and fluorescence spectrum width can be obtained through data of an optical fiber spectrograph. Laser devices of other wavelengths can also be selected by a controller to emit light and the above steps are repeated, then excitation characteristics of fluorescence with different wavelengths can be obtained.

Alzheimer's disease (AD) is a common progressive neurodegenerative disease, and early diagnosis of the disease has always been a problem. More and more researches show that, as early as 10 to 20 years before appearance of AD symptoms, the brain has been subjected to pathological changes. In an early period of AD, β-amyloid proteins are gradually aggregated and deposited, and amyloid plaques are formed in a hypothalamus, an amygdala, an entorhinal cortex, and a hippocampal area, thereby causing tau protein phosphorylation and neurofibrillary tangles, and finally leading to neuron loss, degradation and dementia. After being injected into a blood vessel, a near-infrared fluorescence (NIRF) probe (fluorescent molecule) passes through a blood brain barrier (BBB) and reaches a lesion site for efficient accumulation, at this time, a laser device of 650-1000 nm is selected by a controller to emit light. After the laser passes through an optical fiber guide wire and reaches a lesion tissue, the laser directly irradiates a near-infrared fluorescence (NIRF) probe in the lesion tissue, fluorescence properties (for example, fluorescence strength, fluorescence lifetime, emission wavelength and quantum yield) in β-amyloid protein plaques will be changed dramatically, and the generated efficient fluorescence is collected by an optical fiber guide wire and is transmitted back to a spectrograph for qualitative and quantitative analysis of β-amyloid proteins, thereby realizing early diagnosis of the Alzheimer's disease.

Embodiment 2

With intravascular photodynamic tumor treatment as an example, if a patient suffers from liver cancer, the patient is firstly injected with photosensitive drugs, for example, photophrin, and after keeping out of the sun for a period of time, photosensitizers are concentrated on the tumor site in the liver. Through percutaneous puncture on a blood vessel and under the guidance of clinical imaging, an intravascular puncture needle is delivered and perforates blood vessels inside a liver tumor to reach parenchymal tissues of a tumor, then the intravascular puncture needle is drawn out, a light function guide wire is introduced. The light function guide wire enters into parenchymal tissues of a tumor via a perforated window left by an intravascular puncture needle in the blood vessel inside a tumor, selects photosensitizer to excite a laser at an excitation wavelength of 630 nm to emit light, and the optical fiber guide wire guides the laser device of 630 nm to enter into a tumor which is concentrated with photosensitive drugs, such that the photosensitive drugs inside the tumor are subjected to a photochemical reaction to generate singlet oxygen, and then lead to necrosis and apoptosis of the tumor. When a novel photosensitizer is used for therapy, for example, tetrahydroxybenzene chloride (m-THPC), the absorption peak is at 650 nm, a controller is used to select a laser device of 650 nm to emit light, and the other steps are similar to the above steps.

Embodiment 3

With therapy of cardiovascular and cerebrovascular diseases as another example, cardiovascular and cerebrovascular diseases are diseases with the highest morbidity and mortality. Its basic pathology is atherosclerosis, while root causes of atherosclerosis include an increase of cholesterol, triglyceride and low-density ester protein in the blood and an increase in blood viscosity. Red blood cells of a human body realize an oxygen carrying function through a combination of their own blood proteins and oxygen which enters into a cell membrane. Red blood cells with hyperviscosity and hyperlipidemia are wrapped by an adipose layer and cholesterol, the originally normal red blood cells lose their deformation and oxygen carrying functions, thereby influencing normal delivery of oxygen and leading to hypoxia of human organs and cells. Red photons of 650 nm can increase the number of enzymes (for example, lipoprotein enzyme, cholesterol transferase) which can corrode an adipose layer and cholesterol in the blood, so as to strip an adipose layer which is wrapped outside the red blood cells, thereby improving oxygen carrying and deformation functions of red blood cells, recovering electrification of red blood cells, reducing aggregation of red blood cells, lowering blood lipid, lowering blood viscosity, speeding up blood flow, improve microcirculation, and improve recovery of functions of cerebral nerves and cardiac muscle cells. Through an optical fiber guide wire, red photons of 650 nm can reach any organ and tissue in the human body, thereby being capable of effectively preventing and treating cardiovascular and cerebrovascular diseases.

Figure 2:
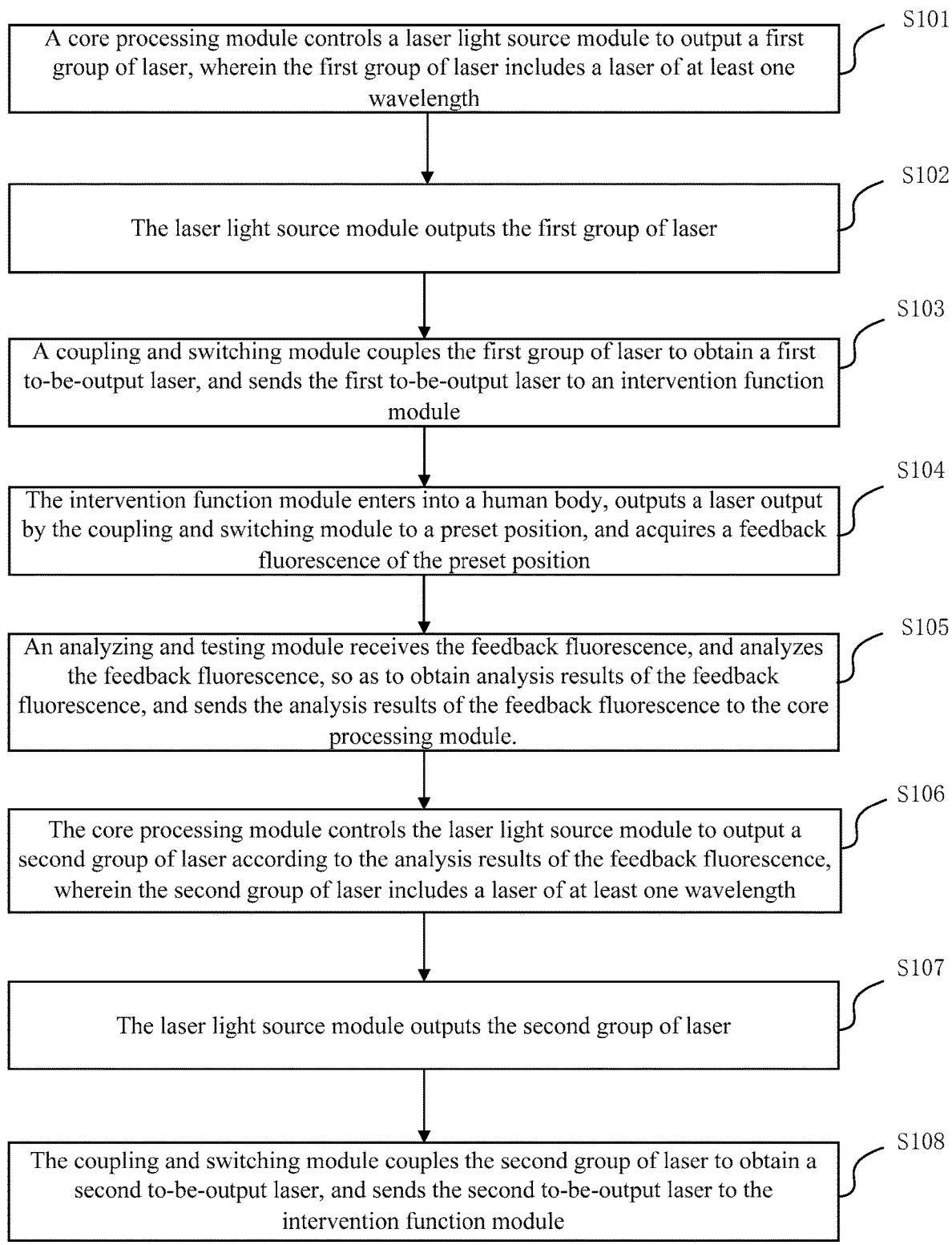
FIG. 2 is a flow chart of an in vivo photon analysis method provided by an embodiment of the present invention.

FIG. 2 shows a flow chart of an in vivo photon analysis method provided by an embodiment of the present invention. The in vivo photon analysis method is applied to the above system. Only the flow of the in vivo photon analysis method is described simply below, and for the other contents which are not described in detail, please refer to related descriptions in the above in vivo photon analysis system. Please refer to FIG. 2, and an in vivo photon analysis method provided by an embodiment of the present invention includes:

S101, a core processing module controls a laser light source module to output a first group of laser, wherein the first group of laser includes a laser of at least one wavelength;

S102, the laser light source module outputs the first group of laser;

S103, a coupling and switching module couples the first group of laser to obtain a first to-be-output laser, and sends the first to-be-output laser to an intervention function module;

S104, the intervention function module enters into a human body, outputs a laser output by the coupling and switching module to a preset position, and acquires a feedback fluorescence of the preset position;

S105, an analyzing and testing module receives the feedback fluorescence, and analyzes the feedback fluorescence, so as to obtain analysis results of the feedback fluorescence, and sends the analysis results of the feedback fluorescence to the core processing module;

S106, the core processing module controls the laser light source module to output a second group of laser according to the analysis results of the feedback fluorescence, wherein the second group of laser includes a laser of at least one wavelength;

S107, the laser light source module outputs the second group of laser; and

S108, the coupling and switching module couples the second group of laser to obtain a second to-be-output laser, and sends the second to-be-output laser to the intervention function module. Then return to perform step S104 of enabling the intervention function module to enter into a human body, outputting a laser output by a coupling and switching device to a preset position, and acquiring a feedback fluorescence of the preset position.

It can be seen that, an in vivo photon analysis method provided by the present invention can penetrate deep into a human body through vascular tunnels inside a human body via a minimally invasive manner, penetrate through a vascular wall and enter into human tissues, extract tissue samples and spectral information of the lesion site, and perform a light therapy on pathological tissues, thereby playing a role of diagnosis and therapy.

Specifically, by utilizing a device (for example, an X-ray, an ultrasound, CT, MRI, etc.) in an image guiding module and under the guidance of clinical imaging, an instrument (for example, a light function guide wire, vascular puncture guide wire) in an intervention function module passes through an artery or vein via percutaneous puncture through a Seldinger puncture intubation technique, and is guided to a blood vessel of a lesion site inside a human body. An intravascular puncture needle reaches nearby the pathological tissue, punctures a vascular wall to enter into the pathological tissue, and samples cells inside the tissue. After an intravascular puncture needle is taken out, an intervention function module is guided to a blood vessel of a lesion site inside a human body in a repeatable manner, such that a first light function guide wire is guided to a puncture site, and enters inside the tissue via a puncture incision. A laser light source module is opened to release laser, a first light function guide wire releases inside the tissue, while the first light function guide wire collects spectral information (such as absorption spectrum, fluorescence spectrum), and conducts to an analyzing and testing module for analysis. After a diagnosis function of a lesion site is completed, the step of guiding an intervention function module to a blood vessel of a lesion site inside a human body is repeated, such that a second light function guide wire is guided to a puncture site, and enters inside the tissue via a puncture incision. A laser light source module is opened to release laser, and a second light function guide wire releases inside the tissue, to perform light therapy on a lesion tissue.

As an optional implementation of an embodiment of the present invention, an in vivo photon analysis method further includes: the displaying and recording module receives analysis results of the feedback fluorescence obtained by the analyzing and testing module, and displays and records the analysis results of the feedback fluorescence. Spectral information is collected through a first light function guide wire, and after the obtained data is further processed by a core processing module, the obtained data is displayed and recorded through a displaying and recording module. Therefore, the analysis results of the feedback fluorescence can be displayed and recorded, so as to facilitate follow-up view and analysis of medical staff.

As an optional implementation of an embodiment of the present invention, an in vivo photon analysis method further includes: the analyzing and testing module acquires the first to-be-output laser, analyzes the first to-be-output laser to obtain analysis results of the first to-be-output laser, and sends the analysis results of the first to-be-output laser to the core processing module; the core processing module controls the laser light source module to output the third group of laser according to analysis results of the first to-be-output laser, wherein the third group of laser includes a laser of at least one wavelength; the laser light source module outputs the third group of laser; and the coupling and switching module couples the third group of laser to obtain a third to-be-output laser, and sends the third to-be-output laser to the intervention function module. Therefore, lasers of different wavelengths for light therapy can be provided according to different situations.

As an optional implementation of an embodiment of the present invention, the in vivo photon analysis method further includes: the displaying and recording module receives the analysis results of the first to-be-output laser obtained by the analyzing and testing module, and displays and records analysis results of the first to-be-output laser, so as to display and record analysis results of the first to-be-output laser, and facilitate follow-up view and analysis of medical staff.

Those skilled in the art should understand that, embodiments of the present application can be provided as methods, systems, or computer program products. Therefore, the present application can be an entirely hardware embodiment, an entirely software embodiment, or an embodiment combining software and hardware. Moreover, the present application can adopt a form of computer program products which can be implemented on one or more computer available storage mediums (which include but are not limited to a disk memory, CD-ROM, and an optical memory) which include computer available program codes.

The application has been described in a flow chart and/or a block diagram of the method, the device (system) and the computer program product according to the embodiments of the application. It shall be appreciated that respective flows and/or blocks in the flow chart and/or the block diagram and combinations of the flows and/or the blocks in the flow chart and/or the block diagram can be embodied in computer program instructions. These computer program instructions can be loaded onto a general-purpose computer, a specific-purpose computer, an embedded processor or a processor of another programmable data processing device to produce a machine so that the instructions executed on the computer or the processor of the other programmable data processing device create means for performing the functions specified in the flow(s) of the flow chart and/or the block(s) of the block diagram.

These computer program instructions can also be stored into a computer readable memory capable of directing the computer or the other programmable data processing device to operate in a specific manner, so that the instructions stored in the computer readable memory create an article of manufacture including instruction means which perform the functions specified in the flow(s) of the flow chart and/or the block(s) of the block diagram.

These computer program instructions can also be loaded onto the computer or the other programmable data processing device, so that a series of operational steps are performed on the computer or the other programmable data processing device to create a computer implemented process, so that the instructions executed on the computer or the other programmable device provide steps for performing the functions specified in the flow(s) of the flow chart and/or the block(s) of the block diagram.

In a typical configuration, a computing device includes one or more central processing units (CPU), an input/output interface, a network interface and an internal storage.

A storage can possibly include a volatile memory, a random access memory (RAM), and/or a non-volatile memory in a computer readable medium, such as a read only memory (ROM) or a flash memory (flash RAM). A storage is an example of a computer readable medium.

Computer readable media includes permanent and non-permanent media and mobile and non-mobile media, and information storage can be realized through any method or technique. Information can be computer readable instructions, data structures, modules of programs or other data. Storage media of a computer for example include but are not limited to: a phase change memory (PRAM), a static random access memory (SRAM), a dynamic random access memory (DRAM), other types of random access memories (RAM), a read-only memory (ROM), an electrically erasable programmable read-only memory (EEPROM), a flash memory or other memory techniques, a compact disc read-only memory (CD-ROM), a digital versatile disc (DVD) or other types of optical storage, and a cassette tape. Tape and disc storage devices or other magnetic storage devices or any other non-transmission media can be used to store information accessed by a computing device. As defined in the text, the computer readable media do not include transitory media, such as modulated data signals and carriers.

What is described above is merely embodiments of the present application, and is not used for limiting the present application. For those skilled in the art, various alterations and changes can be made to the present application. Any modifications, equivalent substitutions and improvements made within the spirit and principle of the present application shall all fall within the scope of claims of the present application.

I claim:

1. An in vivo photon analysis system, comprising: an in vivo device and an in vitro device; wherein
   a) the in vivo device comprises: an intervention function assembly arranged and configured to be placed into a human body, output a laser first output by the in vitro device to a preset position, and acquire a feedback fluorescence of the preset position; and
   b) the in vitro device comprises: a core processing assembly, a displaying and recording assembly, a laser light source assembly, an analyzing and testing assembly, and a coupling and switching assembly; wherein
      i) the laser light source assembly is arranged and configured to output a first group of laser, a second group of laser, and a third group of laser, wherein the first group of laser comprises a laser of at least one wavelength, the second group of laser comprises a laser of at least one wavelength, and the third group of laser comprises a laser of at least one wavelength;
      ii) the coupling and switching assembly is arranged and configured to couple the first group of laser to obtain a first to-be-output laser, and send the first to-be-output laser to the intervention function assembly, couple the second group of laser to obtain a second to-be-output laser, couple the third group of laser to obtain a third to-be-output laser, and send the second to-be-output laser and the third to-be-output laser to the intervention function assembly, so as to acquire the feedback fluorescence, and send the feedback fluorescence to the analyzing and testing assembly;
      iii) the analyzing and testing assembly is arranged and configured to receive the feedback fluorescence, and analyze the feedback fluorescence, so as to obtain analysis results of the feedback fluorescence, and send the analysis results of the feedback fluorescence to the core processing assembly; and
      iv) the core processing assembly is arranged and configured to control the laser light source assembly to output the first group of laser, and control the laser light source assembly to output the second group of laser according to the analysis results of the feedback fluorescence, and is further configured to control the laser light source assembly to output the third group of laser according to analysis results of the first to-be-output laser.

2. The system of claim 1, wherein the in vitro device further comprises:
   a displaying and recording assembly;
      wherein the displaying and recording assembly is configured to receive analysis results of the feedback fluorescence obtained by the analyzing and testing assembly, and display and record the analysis results of the feedback fluorescence.

3. The system of claim 1, wherein the in vitro device further comprises: a displaying and recording assembly;
   the displaying and recording assembly is configured to receive the analysis results of the first to-be-output laser obtained by the analyzing and testing assembly, and display and record analysis results of the first to-be-output laser.

4. An in vivo photon analysis method, comprising:
controlling a laser light source assembly with a core processing assembly to output a first group of laser, wherein the first group of laser comprises a laser of at least one wavelength;
outputting the first group of laser with the laser light source assembly;
coupling the first group of laser to obtain a first to-be-output laser, and sending the first to-be-output laser to an intervention function assembly;
the intervention function assembly entering into a human body, outputting a laser output by a coupling and switching device at a preset position in the human body, and acquiring a feedback fluorescence of the preset position;
receiving and analyzing the feedback fluorescence, so as to obtain analysis results of the feedback fluorescence, and sending the analysis results of the feedback fluorescence to the core processing assembly;
the core processing assembly controlling the laser light source assembly to select and output either a second group of laser or a third group of laser according to the analysis results of the feedback fluorescence, wherein the second group of laser comprises a laser of at least one wavelength and the third group of laser comprises a laser of at least one wavelength different than the wavelength of the second group of laser;
outputting the selected group of laser; and
coupling the selected group of laser to obtain a to-be-output laser, and sending the to-be-output laser to the intervention function assembly, and enabling the intervention function assembly to output the to-be-output laser to the preset position.

5. The method of claim 4, further comprising:
displaying and recording the analysis results of the feedback fluorescence.

6. The method of claim 4, further comprising:
displaying and recording the analysis results of the first to-be-output laser.

* * * * *